(12) United States Patent
Roberson

(10) Patent No.: US 6,254,591 B1
(45) Date of Patent: Jul. 3, 2001

(54) SCAVENGER SUCTION DEVICE

(75) Inventor: David W. Roberson, Chestnut Hill, MA (US)

(73) Assignee: Children's Medical Center Corporation, Boston, MA (US)

( * ) Notice: Subject to any disclaimer, the term of this patent is extended or adjusted under 35 U.S.C. 154(b) by 0 days.

(21) Appl. No.: 09/323,717

(22) Filed: Jun. 1, 1999

(51) Int. Cl.[7] .......................... A61M 1/00; A61M 27/00
(52) U.S. Cl. ........................ 604/541; 128/207.14
(58) Field of Search ................ 604/23, 35, 77, 604/93, 173, 264, 275, 902, 284, 331, 540–541, 322–323, 326–328; 128/207.14, 207.15

(56) References Cited

U.S. PATENT DOCUMENTS

| | | | |
|---|---|---|---|
| 2,450,217 | * | 9/1948 | Alcorn .................................. 128/350 |
| 4,112,936 | * | 9/1978 | Blachly ................................. 128/136 |
| 4,148,308 | * | 4/1979 | Sayer ..................................... 128/15 |
| 4,166,467 | * | 9/1979 | Abramson ............................ 128/351 |
| 4,300,550 | * | 11/1981 | Gandi et al. ..................... 128/207.18 |
| 4,351,328 | * | 9/1982 | Bodai ............................. 128/202.16 |
| 4,364,394 | * | 12/1982 | Wilkinson .............................. 604/96 |
| 4,375,811 | * | 3/1983 | Sabbota et al. ........................ 604/97 |
| 4,449,522 | * | 5/1984 | Baum ............................... 128/200.26 |
| 4,508,533 | * | 4/1985 | Abranson ............................... 604/35 |
| 4,573,965 | * | 3/1986 | Russo ..................................... 604/30 |
| 4,607,635 | * | 8/1986 | Heyden ........................... 128/207.15 |
| 4,637,389 | * | 1/1987 | Heyden . |
| 4,692,153 | * | 9/1987 | Berlin et al. ......................... 604/171 |
| 4,848,331 | * | 7/1989 | Northway-Meyer ............ 128/200.26 |
| 4,862,903 | * | 9/1989 | Campbell ............................. 128/861 |
| 4,865,586 | * | 9/1989 | Hedberg ................................ 604/93 |
| 4,925,452 | * | 5/1990 | Melinyshyn et al. . |
| 5,005,573 | * | 4/1991 | Buchanan ........................ 128/207.14 |
| 5,067,497 | * | 11/1991 | Greear et al. .................... 128/207.15 |
| 5,203,320 | * | 4/1993 | Augustine . |
| 5,255,675 | * | 10/1993 | Kolobow .......................... 128/204.18 |
| 5,381,783 | * | 1/1995 | Hintz ................................ 128/206.29 |
| 5,400,771 | * | 3/1995 | Pirak et al. .............................. 128/6 |
| 5,590,643 | * | 1/1997 | Flam ................................. 128/200.6 |
| 5,599,304 | * | 2/1997 | Shaari ..................................... 604/94 |
| 5,605,147 | * | 2/1997 | Truthan ........................... 128/203.12 |
| 5,694,929 | * | 12/1997 | Christopher ..................... 128/207.14 |
| 5,832,920 | * | 11/1998 | Field ................................ 128/207.14 |
| 5,846,219 | * | 12/1998 | Vancaillie ............................... 604/35 |

* cited by examiner

Primary Examiner—Sharon Kennedy
Assistant Examiner—Catherine Serke
(74) Attorney, Agent, or Firm—Nutter, McClennen & Fish, LLP

(57) ABSTRACT

A medical scavenger suction device includes a tubing assembly having a primary tube and two or more auxiliary tube members. The tubing assembly may be integrally formed within an endotracheal tube sidewall or formed integrally with a mouth gag device. The tubing assembly is adapted to connect to standard wall suction tubing to enable the exhausting of gas and/or smoke from the surgical area.

26 Claims, 6 Drawing Sheets

SCAVENGER SUCTION DEVICE

CROSS-REFERENCE TO RELATED APPLICATIONS

Not Applicable.

STATEMENT REGARDING FEDERALLY SPONSORED RESEARCH

Not Applicable.

FIELD OF THE INVENTION

The invention relates to a suction device, and more particularly, to a scavenger suction device for use during surgery.

BACKGROUND OF THE INVENTION

A patient must be provided with respiratory assistance during surgery under general anaesthesia. It is common practice during such surgical procedures to insert an endotracheal tube into the patient's mouth, through the larynx and into the trachea. The endotracheal tube is then connected to a ventilator to assist breathing. In practice, the endotracheal tube may be used to deliver oxygen and/or anaesthetic gas to the patient. Typically, these endotracheal tubes have at one end a radially expansible cuff, such as an inflatable balloon, which helps to secure and seal the endotracheal tube in the throat.

Cuffless endotracheal tubes are often used in pediatric surgical procedures (e.g., tonsillectomies and adenoidectomies) due to the smaller tracheas of children. Use of the cuffless endotracheal tube can result in retrograde gas leak through the larynx and into the oropharynx. Such gases may include oxygen and nitrous oxide, both of which support combustion. The combination of these gases leaking into the oropharynx may create an environment where combustion is possible, especially when electrocautery procedures are used.

Since electrocautery is used in most pediatric tonsillectomy procedures to seal or cauterize tissue, the use of electrocautery in an enriched oxygenated environment can lead to combustion and resulting catastrophic fires. In addition, electrocautery procedures can generate smoke and thus obscure the surgical field in which the surgeon is operating.

To minimize such dangers, a separate "scavenger" suction device is sometimes used during surgery to suction and exhaust any smoke and/or gas present as a result of retrograde leakage. This separate scavenger suction device must be inserted into the throat area by a nurse or surgeon, thus further crowding the limited area in which the surgeon must operate. Furthermore, if suctioning is not performed, or is not effective to remove all combustible gases, the risk of combustion remains.

It would thus be desirable to provide a device that removes leaking gases during surgery to prevent dangerous combustion and also removes any unwanted smoke produced during surgery without further cluttering the surgical area.

SUMMARY OF THE INVENTION

A scavenger suction device is provided, and at least a portion of the device is adapted for insertion into a patient's oropharynx. The device includes a primary tube member having an open proximal end, a distal end and a generally cylindrical sidewall extending therebetween which defines a lumen. At least one, and preferably at least two, staggered primary tube extension members are provided which extend distally from the primary tube member. The primary tube extension members are preferably arranged in a staggered, spaced-apart fashion and each extension member is preferably of a different length. Each extension member has a generally cylindrical sidewall which defines a lumen with at least one suction port formed in the sidewall which is in communication with the lumen.

The tube assembly may be integrated directly into an endotracheal tube, or it may be formed integrally with a mouth gag device to provide for continual suction of gases and/or smoke during a surgical procedure. A one-way or backcheck valve may be disposed within the tube assembly to prevent backflow of exhausted gas and/or smoke.

BRIEF DESCRIPTION OF THE DRAWINGS

A more complete understanding of the present invention and the attendant advantages and features thereof will be more readily understood by reference to the following detailed description when considered in conjunction with the accompanying drawings wherein.

DETAILED DESCRIPTION OF THE INVENTION

Figure 1:
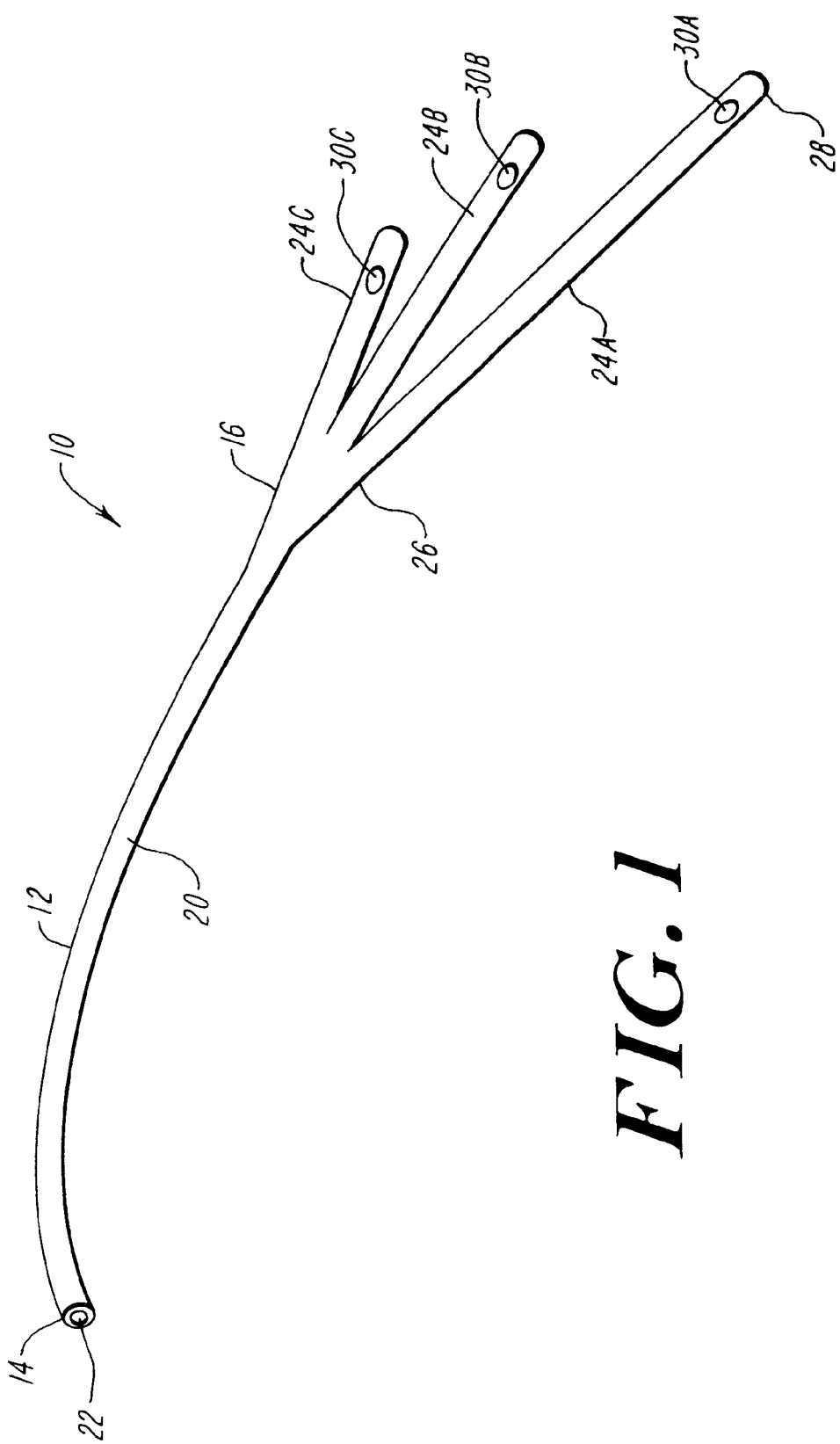
FIG. 1 is a schematic illustration of an embodiment of a scavenger suction tube assembly in accordance with the invention.
Figure 2:
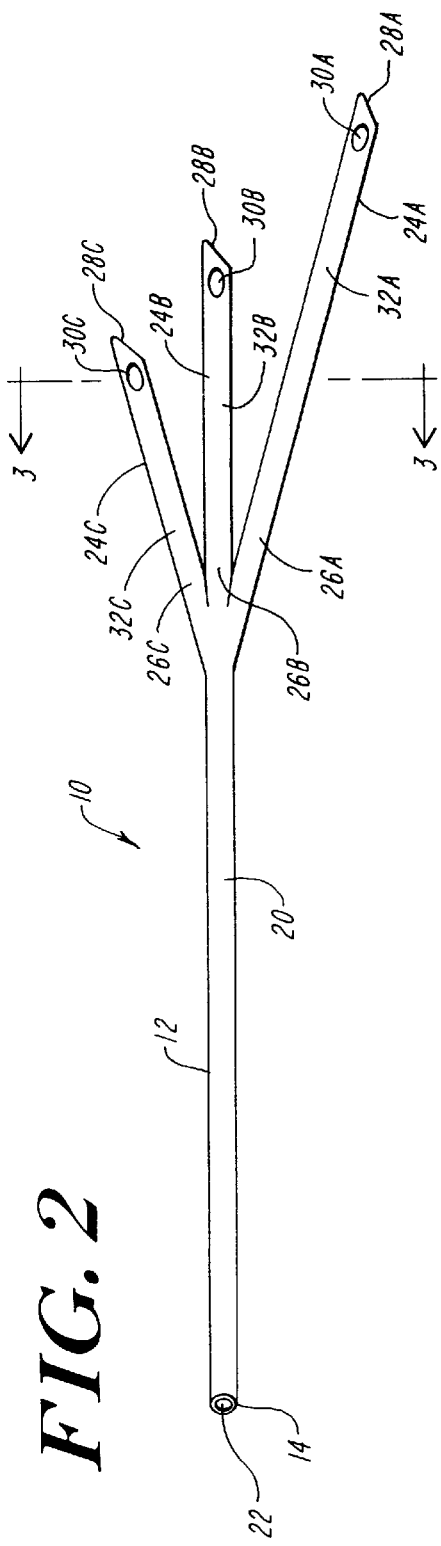
FIG. 2 is a top view of the suction tube assembly of FIG. 1.

FIG. 1 illustrates a scavenger suction tube device or assembly 10 according to the present invention. The scavenger suction tube assembly 10 includes an elongate primary tube member 12 having a proximal end 14 and a distal end 16 with a generally cylindrical sidewall 20 extending therebetween. The sidewall 20 defines a lumen or passageway 22 which extends between the proximal end 14 and the distal end 16 of the primary tube member 12. The tube assembly 10 further includes three primary tube extension members 24A, 24B, 24C, each of which extends distally from the primary tube member 12. As shown in FIG. 2, each primary tube extension member 24A, 24B, 24C has a proximal end 26A, 26B, 26C and a distal end 28A, 28B, 28C with a generally cylindrical sidewall 32A, 32B, 32C extending therebetween. In an exemplary embodiment, the distal ends 28A, 28B, 28C of each primary tube extension member 24A, 24B, 24C have at least one suction port 30A, 30B, 30C formed therein.

Figure 3:
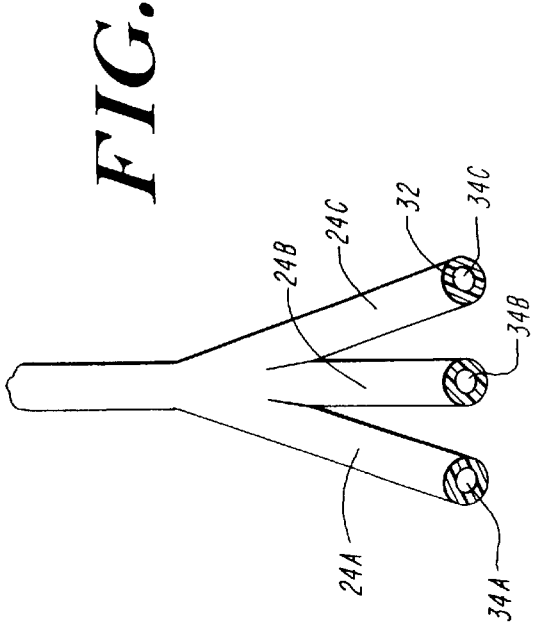
FIG. 3 is a perspective view of a portion of the assembly of FIG. 2, sectioned at line 3—3 in FIG. 2.

Referring now to FIG. 3, each extension member sidewall 32A, 32B, 32C also defines a separate lumen 34A, 34B, 34C within each tube extension member 24A, 24B, 24C. These lumens 34A, 34B, 34C extend from the proximal end 26A, 26B, 26C to the distal end 28A, 28B, 28C of each extension member 24A, 24B, 24C. At the proximal end 26A, 26B, 26C, the lumens 34A, 34B, 34C merge with and are in communication with the primary lumen 22 of the primary tube member 12. Thus, the interconnected lumens form a series of flow paths which extend from the distal ends 28A, 28B, 28C of each primary tube extension member 24A, 24B, 24C through to the proximal end 14 of the primary tube member 12. In operation and upon the application of a vacuum force any gases, fumes or smoke are collected by suction ports 30A, 30B, 30C and are evacuated through lumens 34A, 34B, 34C to lumen 22 and are exhausted out the proximal end 14 of the primary tube member 12, as discussed below.

In an exemplary embodiment, the tube extension members 24A, 24B, 24C are of varying lengths and are positioned in a staggered, spaced-apart fashion. The tube extension members may range from about 1 to 5 cm in length and may be spaced apart from one another in the range of about 2 to 10 mm. The length of the tubes, as well as distances by which they are spaced apart, may vary depending upon the requirements of a given application. By way of example, the entire length of tubing assembly, including the tube extension members, can be between about 6 to 10 inches. Furthermore, in an exemplary embodiment, the primary tube member may have a diameter in the range of about 5 to 10 mm and the extension tube members have a diameter in the range of about 1 to 4 mm.

The suction tube assembly preferably is manufactured from a material that is suitable for use in surgical and medical procedures. The material can be flexible, but should have sufficient rigidity to be able to withstand forces typically incurred while using suction equipment common to operating rooms. One of ordinary skill in the art can readily ascertain the identity of suitable materials. Medical grade polymers are among the more preferred materials.

Although only three primary tube extension members are illustrated, it is contemplated that less than three or more than three may be used in accordance with the teachings of the present invention. It is also contemplated that a single extension or auxiliary tube may be used, but the use of at least two extension or auxiliary tubes decreases the likelihood that any clogging or blockage may occur in the tubing assembly.

As described above, the tube extension members 24A, 24B and 24C are formed as direct extensions branching off from the primary tube member 12. However, the tube extension members may also be separately formed and may be attached by a multi-port coupling, not shown, to the primary tube member. A variety of mechanisms may be used to couple the tube extension members to the primary tube member, including interference fit arrangements, threaded connectors, and bayonet-type connectors.

Figure 4:
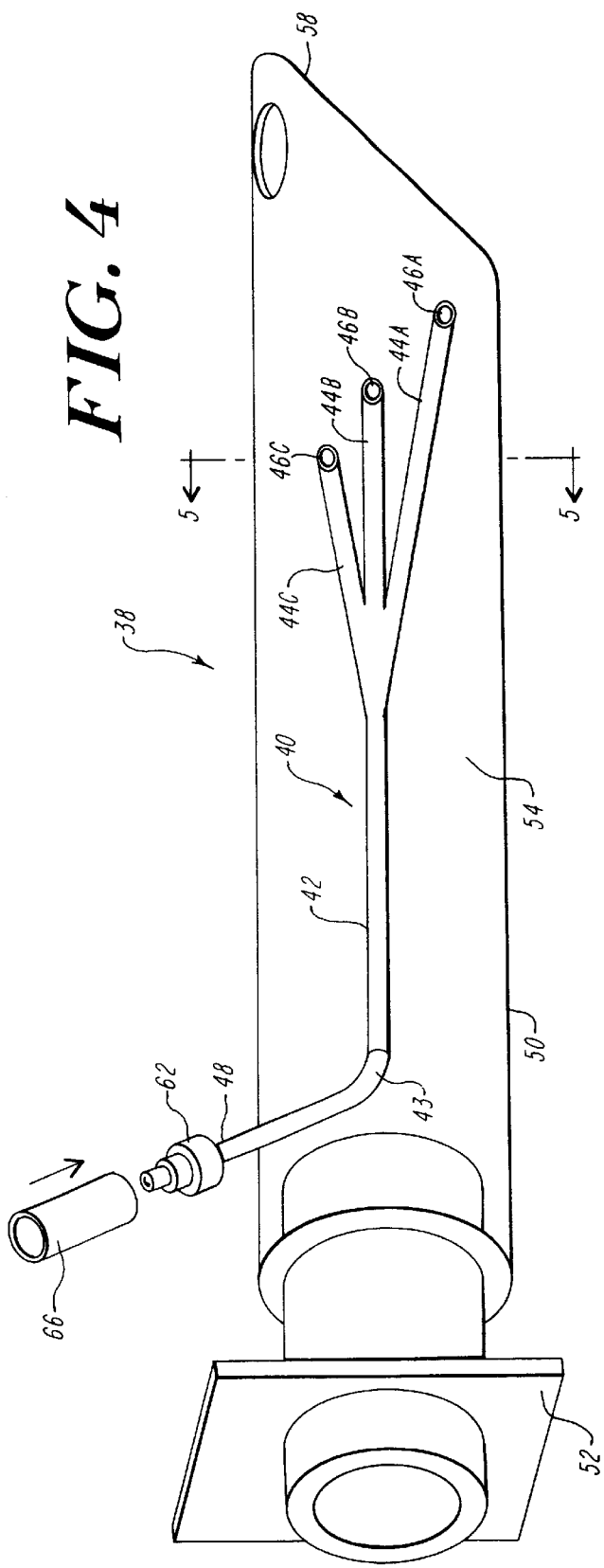
FIG. 4 illustrates an embodiment of the tube assembly of the present invention disposed within an endotracheal tube sidewall.

FIG. 4 illustrates a device 38 which integrates an embodiment of the scavenger suction assembly 40 of the present invention with an endotracheal tube 50. In this embodiment, the scavenger suction assembly 40 includes a primary tube member 42 and three auxiliary tube members 44A, 44B, 44C which have terminal openings 46A, 46B, 46C formed in their respective distal ends. In a variation of this embodiment, the terminal openings 46A, 46B, 46C may be formed proximate the distal ends, such as in the form of an opening in the sidewall of the auxiliary tube members in the manner illustrated in FIG. 1.

Figure 5:
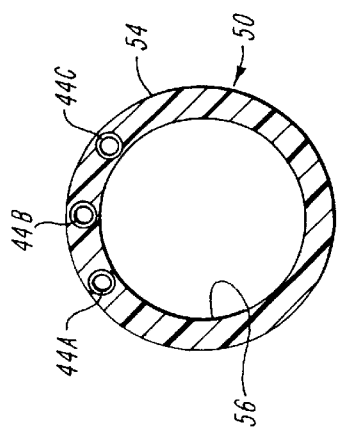
FIG. 5 is a sectional view of the device of FIG. 4 taken along line 5—5.

As shown in FIG. 4, the primary tube member 42 and auxiliary tube members 44A, 44B, 44C are integrally formed within the sidewall of a cuffless endotracheal tube 50. In an exemplary embodiment, the endotracheal tube 50 includes a collar portion 52 which facilitates connection to a ventilator or other conventional breathing apparatus. As shown in FIG. 5, the endotracheal tube 50 further has a generally cylindrical sidewall which includes an outer sidewall surface 54 and an inner sidewall surface 56 which both extend from the collar portion 52 to an open distal end 58 of the endotracheal tube 50. In this embodiment, a portion of the length of the primary tube member 42 and the entire length of the auxiliary tube members 44A, 44B, 44C are disposed between the outer sidewall 54 and the inner sidewall 56. A proximal portion 43 of the primary tube member 42 protrudes from the endotracheal sidewall to facilitate connection to a suction source as discussed below.

Figure 6:
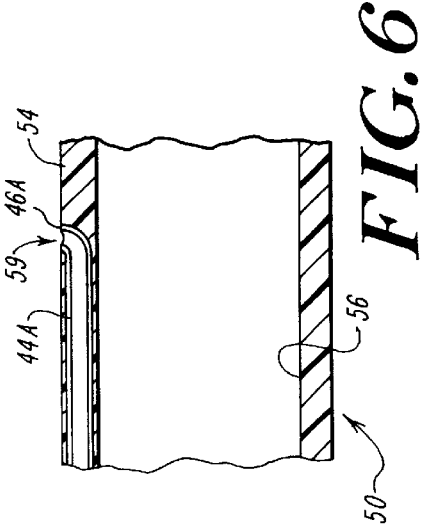
FIG. 6 is a detailed cross sectional view of the suction tube integrated into an endotracheal tube sidewall.

In an exemplary embodiment, terminal openings 46A, 46B, 46C formed at the distal ends of auxiliary tube members 44A, 44B, 44C exit the outer sidewall surface 54 through corresponding openings formed within the outer sidewall surface 54. For example, as shown in FIG. 6, the opening 46A of auxiliary tube member 44A aligns with an opening 59 formed in the outer sidewall surface 54 of the endotracheal tube 50. Thus, any gas or smoke present in the operating area may be suctioned in through opening 59 and up through the auxiliary tube member 44A. As shown in FIG. 4, the auxiliary tube members 44A, 44B, 44C are positioned in a staggered configuration along the endotracheal sidewall to prevent unwanted clogging of the tube assembly as discussed earlier herein.

In an exemplary embodiment, such as shown in FIG. 4, the primary tube member 42 has a suction hose coupling 62 attached at a proximal end 48 thereof. The suction hose coupling 62 has a graduated tapered sidewall construction adapted to connect to suction hoses 66 having a variety of diameters. The suction hose 66 preferably connects to a standard wall-mounted suction source, not shown, which is present within operating rooms and which is adapted to vent the gas and/or smoke out of the room and/or building. Alternatively, the suction hose can communicate with a portable suction unit which likewise is adapted to create a suction force and to convey exhausted gases out of the operating room. The magnitude of the suction force can be regulated directly by the suction source or by a device adjacent the suction hose 66, such as a roller clamp (not shown) which restricts gas flow within the hose.

Figure 7:
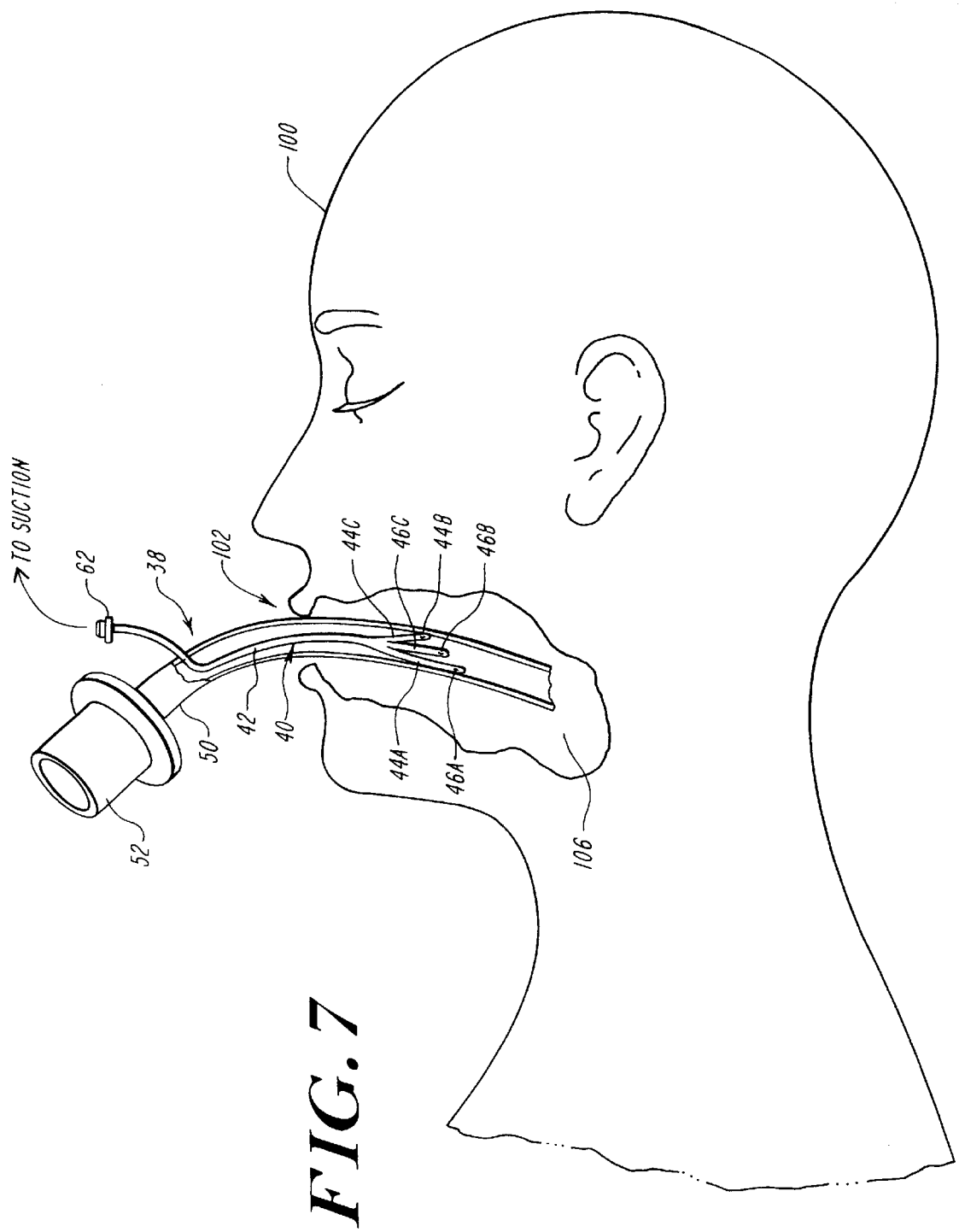
FIG. 7 illustrates a portion of the device of FIG. 6 in a patient's throat.

Referring to FIG. 7, the device shown in FIGS. 4–6 is shown placed within a patient's throat in a manner that is common during tonsil or adenoid surgery. The device 38 is placed into the patient's mouth 102 and positioned within the oropharynx 106. Preferably, the device 38 is inserted to a depth such that the auxiliary tube members 44A, 44B, 44C are positioned within the oropharynx 106 and the primary tube member 42 protrudes partially out of the patient's mouth 102. In operation, the endotracheal cuff 52 is connected to a ventilator apparatus (not shown) and the tubing assembly 40 is then connected to a suction source (not shown) through coupling 62. As so connected, the primary tube member 42 and auxiliary tube extension members 44A, 44B, 44C, through suction ports 46A, 46B, 46C, cooperate to remove any gas or smoke in the oropharynx 106 present during a surgical procedure.

Figure 8:
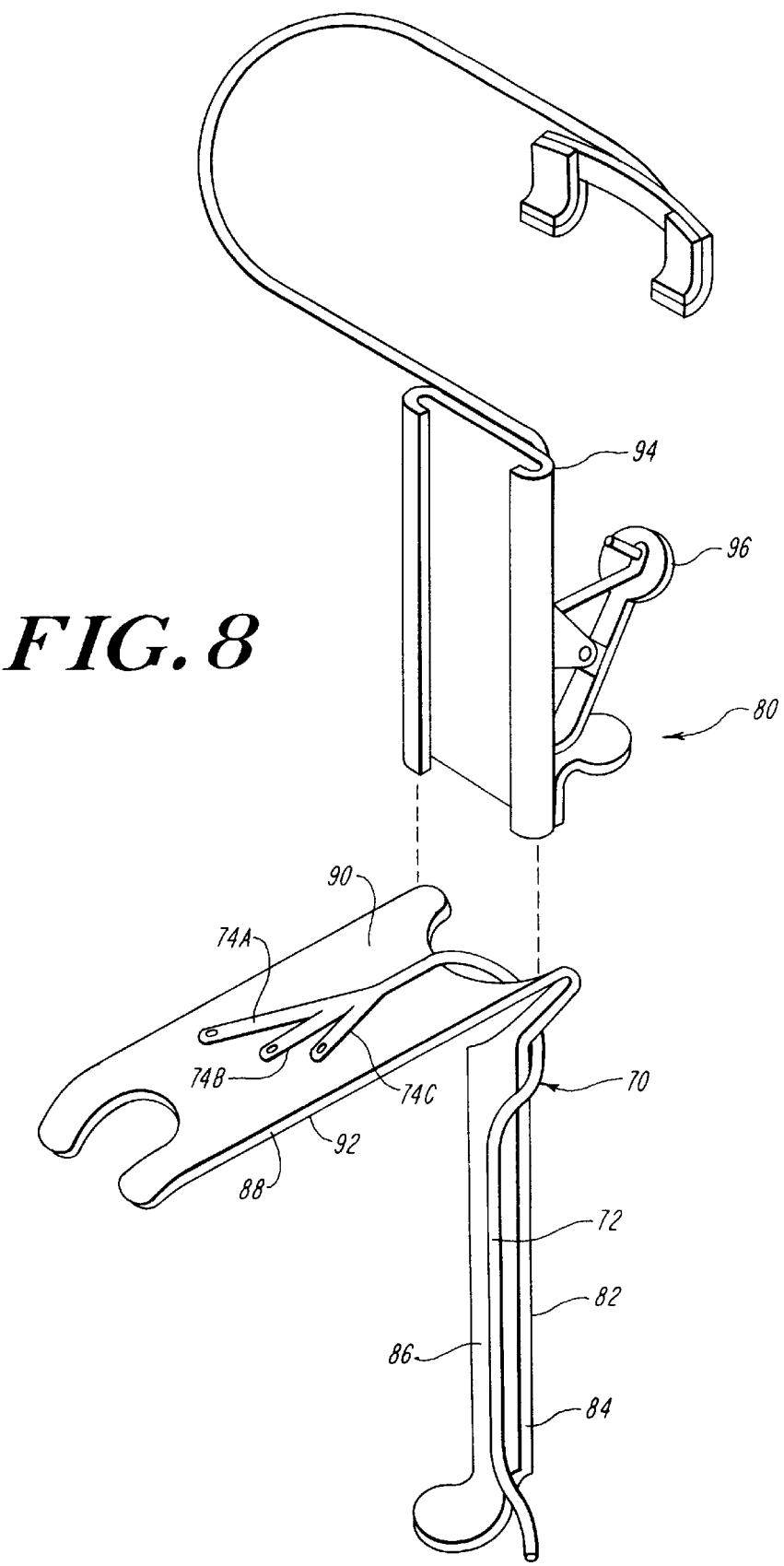
FIG. 8 illustrates another embodiment of the present invention wherein the tube assembly is integrated with a mouth gag device.

FIG. 8 illustrates a mouth gag device 80 integrating an embodiment of the tube assembly 70 of the present invention. In this embodiment, the tube assembly 70 is integrated into a mouth gag device 80 which is adapted for holding a patient's mouth open and securing the tongue during surgery. The mouth gag device 80 includes a handle portion 82, a tongue plate 88 and an adjustment portion 94. The handle portion 82 has a superior surface 84 and an inferior surface 86 which both provide for slidable movement of the adjustment portion 94. Adjustment of the device is provided by an adjustment lever 96, which is typically depressed to release the adjustment portion 94 from the handle portion 82. The adjustment portion 94 is then free to slide along the handle portion to accommodate patients of different sizes.

Figure 9:
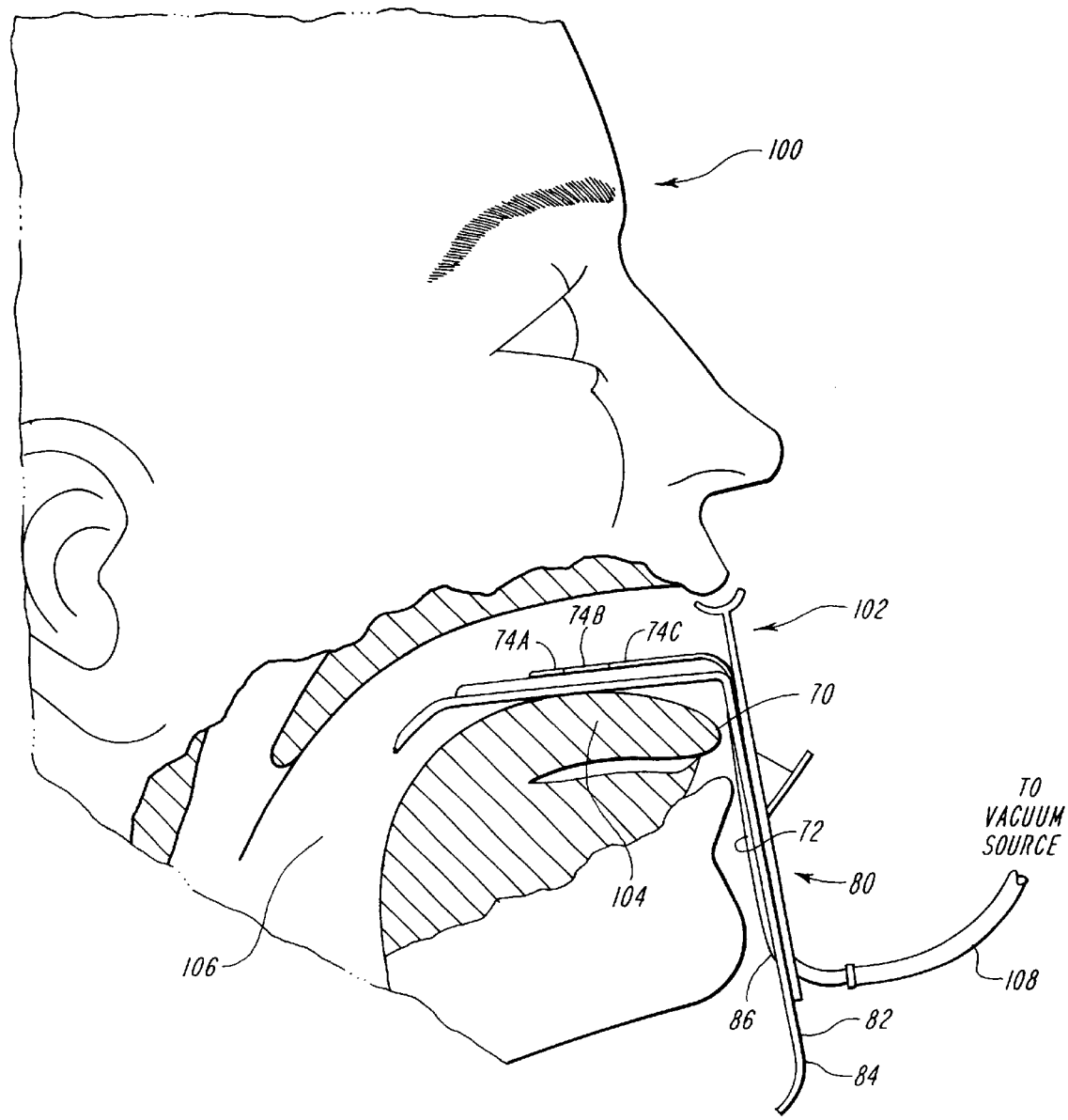
FIG. 9 illustrates the device of FIG. 8 in a patient's mouth.

The mouth gag device 80 further includes a tongue plate 88 which has a superior surface 90 and an inferior surface 92 which holds and secures the tongue 104 during a surgical procedure, as shown in FIG. 9. In an exemplary embodiment, the primary tube member 72 is integrally formed on the inferior surface 86 of the handle portion 82 and the extension members 74A, 74B, 74C are integrally formed on the superior surface 90 of the tongue plate 88. In an exemplary embodiment, the primary tube member 72 and primary tube extension members 74A, 74B, 74C are made of the same material as the mouth gag 80, such as a stainless steel or titanium. One of ordinary skill in the art will readily appreciate that the tube assembly may alternatively be affixed or attached as a separate component to the mouth gag.

Referring to FIG. 9, the device of FIG. 8 is shown in position in a patient's mouth. During a surgical procedure, the patient 100 is intubated in the usual manner using a standard endotracheal tube (not shown). The mouth gag 80, such as shown in FIG. 9, is then inserted into the mouth 102 of the patient 100. The tube assembly 70 is then connected to a suitable vacuum source via a suction hose 108, and the vacuum source is activated. As anesthesia gas is delivered to the patient through the endotracheal tube, any leaked gas and/or smoke which is present within the oropharynx 106 is suctioned through the scavenger tube assembly 70 and vented to the outside of the operating room.

In other embodiments of the present invention, a one-way valve, not shown, may be disposed within either or both the primary tube member and/or the extension or auxiliary tube members to provide for the flow of gas within the tubing assembly only in a direction away from the patient. Such a valve may be useful in the case of an accidental connection of the scavenger tubing assembly to something other than a suction hose, such as an oxygen source.

As used herein, the terms "assembly" and "device" are intended to encompass any surgical implement used in association with human or animal medical treatment, diagnosis, study, or analysis. More particularly, a surgical device is intended to encompass any implement or portion thereof that is entirely or partially inserted into a human or animal body by any means of entry, such as through a natural body orifice, an incision, or a puncture. The term surgical device is not intended to connote a limitation to treatment of a single body system, organ, or site.

One skilled in the art will appreciate further features and advantages of the invention based on the above-described embodiments. Accordingly, the invention is not to be limited by what has been particularly shown and described, except as indicated by the appended claims.

What is claimed is:

1. An elongate suction tube assembly, comprising:
   a primary tube member having an open proximal end, a distal end and a generally cylindrical sidewall extending therebetween, and having a diameter in the range of about 5 to 10 mm; and
   at least two primary tube extension members extending from the distal end of the primary tube member, each of the extension members having a different length, a diameter in the range of about 1 to 4 mm, and a sidewall with at least one suction port formed therein,
      wherein at least a portion of the assembly is insertable into a patient's oropharynx to suction airborne matter therefrom, wherein the primary tube member and the at least two extension members are integrally formed within an endotracheal tube having an outer sidewall and an inner sidewall, such that the primary tube member and the at least two extension members are disposed between the outer and inner sidewalls of the endotracheal tube, and wherein each of the at least two extension members directly communicates with a region outside of the endotracheal tube and within the patient's oropharynx.

2. The assembly of claim 1, wherein the primary tube member and the at least two extension members are integrally formed on a mouth gag device having a handle portion and a tongue plate, such that the primary tube member is disposed along the handle portion and each of the at least two primary tube extension members is disposed along the tongue plate.

3. The assembly of claim 2, wherein the primary tube member is disposed on an inferior surface of the handle portion and each of the at least two extensions members is disposed on a superior surface of the tongue plate.

4. The assembly of claim 1, further comprising a coupling joined to the proximal end of the primary tube member, the coupling being adapted to connect to a source of a vacuum force.

5. The assembly of claim 1, wherein each of the tube extension members is made of a gas impermeable plastic.

6. The assembly of claim 1, further comprising a one-way valve disposed within the primary tube member and adapted to permit gas to flow only in a direction away from the patient.

7. A surgical inter-orifice gas suction device, comprising:
   a primary tube member having a proximal end, a distal end and a sidewall extending therebetween and defining a primary suction flow path of the primary tube member;
   at least two auxiliary tube members extending from the distal end of the primary tube member and having a sidewall defining at least one suction port, wherein each of the at least two auxiliary tube members defines a separate auxiliary suction flow path which is in communication with the primary suction flow path; and
   a housing member, adapted for insertion into a patient's throat during a surgical procedure, on which the primary tube member is disposed so that each of the at least one suction ports directly communicates with a region outside of the housing and within the patient's throat.

8. The device of claim 7, wherein the housing member is an endotracheal tube.

9. The device of claim 7, wherein the endotracheal tube is cuffless and has a proximal end, a distal end and a sidewall extending therebetween, and wherein the primary tube member and each of the at least two auxiliary tube members are disposed between an inner surface and an outer surface of the sidewall of the cuffless endotracheal tube.

10. The device of claim 8, wherein each of the at least two auxiliary tube members is of a different length and each is positioned in a staggered, spaced apart fashion within the tube sidewall of the endotracheal tube.

11. The device of claim 10, wherein each of the at least two auxiliary tube members is spaced apart from one another by a distance in the range of about 2 to 10 mm.

12. The device of claim 11, wherein the outer surface of the sidewall of the endotracheal tube has openings formed therein, wherein each of the openings coincides with a suction port of one of the at least two auxiliary tube members.

13. The device of claim 7, wherein the housing member is a mouth gag having a tongue plate, wherein each of the at least two auxiliary tube members are integrally formed on a superior surface of the tongue plate.

14. The device of claim 13, wherein the primary tube member and each of the at least two auxiliary tube members are made of an identical material as the mouth gag.

15. The device of claim 7, wherein the proximal end of the primary tube member includes a coupling adapted to connect the primary tube member to a wall suction tube.

16. The device of claim 7, wherein the primary tube member and each of the at least two auxiliary tube members are made of a gas impermeable plastic.

17. The device of claim 7, wherein the primary tube member has a diameter in the range of about 5 to 10 mm and each of the at least two auxiliary tube members have a diameter in the range of about 1 to 4 mm.

18. The device of claim 7, wherein each of the at least two auxiliary tube members has a length in the range of about 1 to 5 cm.

19. The device of claim 7, wherein the housing comprises a mouth gag device.

20. A method of suctioning airborne matter from within a patient's throat, comprising the steps of:

introducing a treatment system into the patient's throat, the system including:
an endotracheal tube having a proximal end, a distal end, and a sidewall extending from the proximal to the distal end defining an endotracheal lumen; and
a primary suction tube communicating with at least two extension tubes, each extension tube having at least one suction port directly communicating with an area within the patient's throat; and suctioning airborne matter from within the patient's throat into at least one of the suction ports via a suction force.

21. The method of claim 20, wherein the airborne matter is suctioned outside of the endotracheal tube.

22. The method of claim 21, wherein the suction tube is integrally formed within a sidewall of the endotracheal tube.

23. The method of claim 20, wherein the endotracheal tube is cuffless.

24. The method of claim 20, wherein the treatment system further includes a mouth gag device in communication with the primary suction tube.

25. The method of claim 20, wherein each of the at least two extension tubes has a different length.

26. The method of claim 20, wherein the primary suction tube has a diameter in the range of about 5 to 10 mm, and each of the at least two extension tubes has a diameter of about 1 to 4 mm.

* * * * *